United States Patent
Farkas et al.

(10) Patent No.: US 6,767,320 B2
(45) Date of Patent: Jul. 27, 2004

(54) LASER ENDOSCOPE WITH SAFETY DEVICE

(75) Inventors: Richard A. Farkas, Bloomfield Hills, MI (US); Terrance R. Boyd, Jackson, MI (US); Juan F. Velazquez, Saline, MI (US)

(73) Assignee: Inner Vision Imaging, L.L.C., Farmington Hills, MI (US)

( * ) Notice: Subject to any disclaimer, the term of this patent is extended or adjusted under 35 U.S.C. 154(b) by 0 days.

(21) Appl. No.: 10/217,511

(22) Filed: Aug. 13, 2002

(65) Prior Publication Data

US 2004/0034277 A1 Feb. 19, 2004

(51) Int. Cl.[7] .............................................. A61B 1/06
(52) U.S. Cl. ...................................... 600/108; 600/118
(58) Field of Search ................................ 600/108, 118, 600/103, 476, 477; 606/11, 12

(56) References Cited

U.S. PATENT DOCUMENTS

| | | | | |
|---|---|---|---|---|
| 4,422,457 A | * | 12/1983 | Hattori | 606/2 |
| 4,543,477 A | * | 9/1985 | Doi et al. | 250/227.11 |
| 5,154,707 A | * | 10/1992 | Rink et al. | 606/12 |
| 5,409,481 A | * | 4/1995 | Poppas et al. | 606/12 |
| 5,419,312 A | * | 5/1995 | Arenberg et al. | 600/108 |
| 6,511,422 B1 | * | 1/2003 | Chatenever | 600/180 |
| 6,556,851 B1 | * | 4/2003 | Ott et al. | 600/310 |

* cited by examiner

Primary Examiner—John P. Leubecker
(74) Attorney, Agent, or Firm—Gifford, Krass, Groh, Sprinkle, Anderson & Citkowski, P.C.

(57) ABSTRACT

An endoscope assembly includes a housing having an outwardly extending tube with the free end adapted for insertion into a body cavity. A laser is contained within the housing which emits an output beam through the free end of the tube. A light sensor detects light in a predetermined color range which impinges upon the free end of the tube and generates an output signal representative thereof. A circuit disables the laser in response to the output signal from the light sensor.

3 Claims, 1 Drawing Sheet

LASER ENDOSCOPE WITH SAFETY DEVICE

BACKGROUND OF THE INVENTION

I. Field of the Invention

The present invention relates to an endoscope assembly for use in medical procedures.

II. Description of Related Art

There are many previously known endoscopes. Such endoscopes typically comprise a housing having an elongated tube with a free end. The free end of the tube is insertable into a body cavity while an optical system contained in the tube transmits light or other electromagnetic waves from the body cavity, through the tube, so that the interior of the body cavity can be viewed exteriorly of the body.

In order to obtain a view of the interior of the body cavity, it is necessary with these previously known endoscopes to transmit the light or other radiation, such as infrared radiation, (hereinafter collectively referred to as light radiation) through the tube and into the body cavity. The reflected light radiation then passes through the free end of the tube and the optical system contained in the tube for viewing exteriorly of the body.

While different forms of light sources may be used to transmit the light radiation into the body cavity, some modern endoscopes utilize a laser as the light radiation source.

A safety concern arises, however, with the previously known endoscopes which utilize a laser as the light radiation source. Specifically, due to the coherent wave emission inherent with a laser, the laser radiation may cause injury to the medical personnel in the operatory upon removal of the free end of the endoscope tube from the body cavity. Such injury can be particularly serious if the laser output is unintentionally directed into the eyes of the medical personnel.

While it is possible to avoid injury from the laser radiation upon removal of the endoscope tube from the body cavity by simply turning off the laser, mistakes can happen where the laser remains activated despite removal of the endoscope tube from the body cavity.

SUMMARY OF THE PRESENT INVENTION

The present invention provides an endoscope assembly which overcomes the above-mentioned disadvantages of the previously known devices.

In brief, the endoscope assembly of the present invention comprises a housing having a tube with a free end adapted for insertion into a body cavity. The tube contains a conventional optical system to not only convey light radiation into the body cavity, but to also return the reflected light radiation from the body cavity and through the tube for viewing exteriorly of the body.

The endoscope assembly further includes a laser which emits a light radiation output beam through the free end of the tube. The laser preferably emits radiation in the infrared range, although lasers of different wavelength outputs may alternatively be used.

A light sensor is contained within the housing for detecting light of a predetermined color range, e.g. the color green, which impinges at the free end of the endoscope tube. Furthermore, when the light sensor detects light in the predetermined color range, the light sensor generates an output signal.

The endoscope assembly further comprises a circuit which receives the output signal from the light sensor as an input signal. The circuit, upon receipt of the output signal from the light sensor, generates an output signal to disable the laser. As used herein, disabling the laser means to prevent the light radiation from the laser from emitting from the free end of the endoscope tube.

Assuming that the predetermined color range is green, in operation once the tube is inserted into the body cavity the laser operates in the normal fashion to transmit light radiation into the body cavity while the reflection of that light radiation is returned through the endoscope tube for imaging exteriorly of the body. Furthermore, since the laser generates an output signal outside the predetermined color range, no light radiation within the predetermined color range is conveyed back through the endoscope tube for viewing exteriorly of the body.

Conversely, upon removal of the free end of the endoscope tube from the body cavity, the free end of the endoscope tube is exposed to light in the operatory. As a practical matter, light within the predetermined color range, e.g. green light, is common in operatories. As such, the light sensor detects the light within the predetermined range immediately upon removal of the endoscope tube from the body cavity thus activating the circuit to disable the laser.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
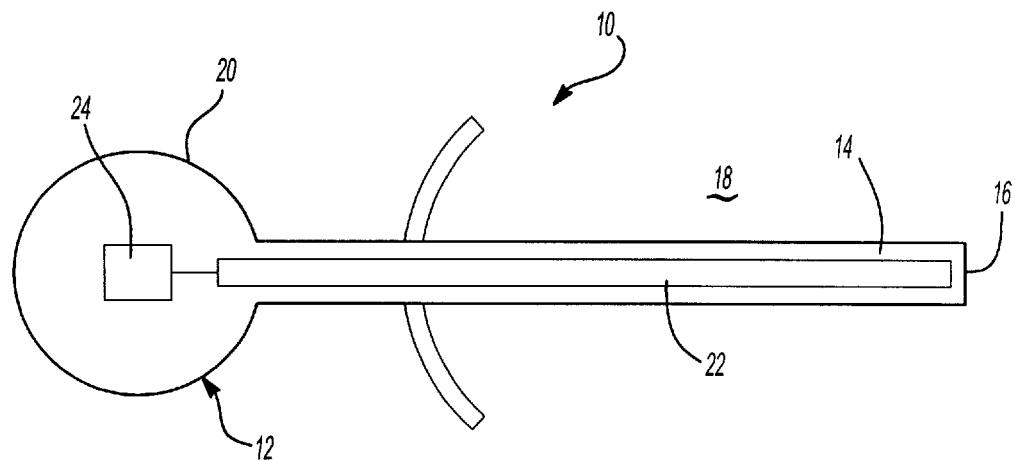
FIG. 1 is a diagrammatic view illustrating a preferred embodiment of the present invention.

With reference first to FIG. 1, an endoscope assembly 10 of the present invention is shown having a housing 12. The housing 12 includes an elongated tube 14 having a free end 16 adapted for insertion into a body cavity 18. The endoscope housing 12 also includes a portion 20 which remains exterior of the body cavity 18. This housing portion 20 may be either manipulated by hand, by robot or otherwise.

In the conventional fashion, the endoscope tube 14 includes an internal optical system 22 for transmitting light radiation, including infrared radiation, not only from the housing portion 20 and out through the free end 16 of the tube 14, but for also conveying reflected light radiation within the body cavity 18 back through the free end 16 of the tube 14, the optic system 22 and to the housing portion 20 for viewing in any conventional manner exteriorly of the body cavity 18.

Figure 2:
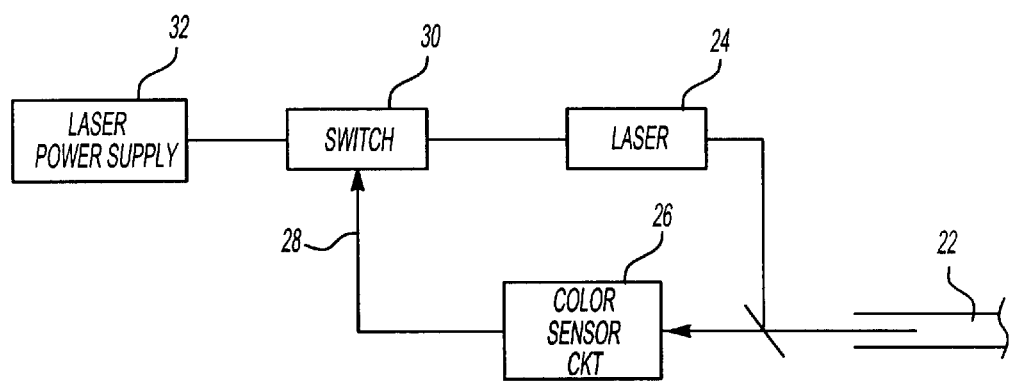
FIG. 2 is a circuit diagram illustrating a portion of the preferred embodiment of the present invention.

With reference now to FIGS. 1 and 2, a laser 24 forms the light radiation source for the endoscope assembly 10. The laser 24 is illustrated only diagrammatically and has its output optically coupled with the optical system 22 in the endoscope tube 14. Thus, upon activation of the laser 24, the laser 24 emits its light radiation out through the end 16 of the endoscope tube 14.

A light sensor circuit 26 is also contained within the housing 12 and preferably within the housing portion 20 and is optically coupled with the optical system 22 in any conventional fashion. The light sensor circuit 26 is adapted to generate an output signal whenever it detects light within a predetermined color range, such as the color green. This output signal, furthermore, is generated along an output 28 from the light sensor circuit 26.

The light detector output 28 is coupled to a circuit, such as an electronic switch 30, which is used to selectively activate or disable the laser 24. As shown in FIG. 2, the electronic switch 30 is preferably electrically connected between a power supply 32 for the laser and the laser 24. The electronic switch 30 is normally closed, thus activating the laser 24. However, in the event that the light sensor circuit 26 detects light within the predetermined range, the light sensor circuit 26 generates an output signal on its output 28 to activate the electronic switch 30 to an open position thus disabling the laser 24. Other conventional means, such as a shutter system, may alternatively be used to disable the laser 24, i.e. to prevent the laser 24 from emitting its output out the free end 16 of the endoscope tube 14.

In operation, when the free end 16 of the endoscope tube 14 is positioned within the body cavity, the laser 24, which generates an output signal outside the predetermined color range of the light sensor circuit 26, emits light radiation through the optical system 22 and into the body cavity 18 through the free end 16 of the endoscope tube 14. The reflected light radiation, which by definition excludes the predetermined color range, is conveyed through the free end 16 of the endoscope tube 14, the optical system 22 and back to the housing portion 20 for viewing exteriorly of the body cavity 18.

Conversely, upon removal of the end 16 of the endoscope tube from the body cavity 18, light within the predetermined color range, i.e. light in the medical operatory, passes through the free end 16 of the endoscope tube 14, through the optical system 22 and is detected by the light sensor circuit 26. The light sensor circuit 26 then immediately activates the electronic switch 30 to an open position thereby disabling the laser 24.

From the foregoing, it can be seen that the present invention provides a simple and yet effective means for selectively disabling the light source from an endoscope upon removal of the endoscope from a body cavity. Having described my invention, however, many modifications thereto will become apparent to those skilled in the art to which it pertains without deviation from the spirit of the invention as defined by the scope of the appended claims.

We claim:

1. An endoscope assembly comprising:

a housing having a tube with a free end adapted for insertion into a body cavity;

a light sensor circuit for detecting light of a predetermined color range of visible light at said free end of said tube, said light sensor circuit generating an output signal whenever said sensor circuit detects visible light in said color range;

a laser switchable between an activated state and a non-activated state, wherein said laser emits an output beam at a wavelength outside said predetermined color range through said free end of said tube only when laser is in said activated state; and a circuit which switches said laser to said non-activated state in response to said output signal from said light sensor circuit.

2. The invention as defined in claim 1 wherein said color range comprises the color green.

3. The invention as defined in claim 1 wherein said circuit comprises an electronic switch.

* * * * *